(12) United States Patent
Kruetzfeldt et al.

(10) Patent No.: US 10,329,066 B2
(45) Date of Patent: Jun. 25, 2019

(54) VISUALIZATION DEVICE FOR USE WITH A TRAY FOR LOADING A MEDICAL DEVICE

(71) Applicant: Medtronic CV Luxembourg S.a.r.l., Luxembourg (LU)

(72) Inventors: Dawn Kruetzfeldt, Santa Rosa, CA (US); Glenn Stante, Santa Rosa, CA (US); Sameer Upadhyaya, Santa Rosa, CA (US)

(73) Assignee: Medtronic CV Luxembourg S.a.r.l., Luxembourg (LU)

( * ) Notice: Subject to any disclaimer, the term of this patent is extended or adjusted under 35 U.S.C. 154(b) by 377 days.

(21) Appl. No.: 14/935,589

(22) Filed: Nov. 9, 2015

(65) Prior Publication Data

US 2016/0058522 A1 Mar. 3, 2016

Related U.S. Application Data

(62) Division of application No. 13/658,082, filed on Oct. 23, 2012, now Pat. No. 9,211,162.

(51) Int. Cl.
*A61F 2/00* (2006.01)
*B65D 77/24* (2006.01)
*A61F 2/24* (2006.01)
*A61B 90/00* (2016.01)
*A61F 2/95* (2013.01)

(52) U.S. Cl.
CPC ............ *B65D 77/24* (2013.01); *A61B 90/361* (2016.02); *A61F 2/2427* (2013.01); *A61F 2/2436* (2013.01); *A61B 2090/3616* (2016.02); *A61B 2090/3618* (2016.02); *A61F 2/0095* (2013.01); *A61F 2002/9522* (2013.01); *B65D 2201/00* (2013.01)

(58) Field of Classification Search
USPC ............... 206/363, 364, 365, 370, 205, 210; 604/523, 528
See application file for complete search history.

(56) References Cited

U.S. PATENT DOCUMENTS

| | | | |
|---|---|---|---|
| 2,084,292 A | 6/1937 | Steiner | |
| 2,099,122 A | 11/1937 | Kreisler | |
| 3,592,201 A * | 7/1971 | Haddaway | A45D 40/22 132/301 |
| 4,555,020 A | 11/1985 | Campello et al. | |
| 5,019,124 A * | 5/1991 | Flugger | B65D 1/36 206/560 |
| 5,586,653 A | 12/1996 | Taveroff | |
| 5,638,839 A | 6/1997 | Montoli | |
| 6,614,604 B1 | 9/2003 | Budde | |

(Continued)

*Primary Examiner* — Jacob K Ackun
(74) *Attorney, Agent, or Firm* — Medler Ferro Woodhouse & Mills PLLC

(57) ABSTRACT

A visualization device for use with a loading tray includes a frame comprising a floor, a first side wall extending generally perpendicular from the floor, and a second side wall extending generally perpendicular from the floor and spaced from the first side wall. The visualization device further includes a mirror abutting the floor of the frame. A magnifying glass may also be supported by top edges of the first and second side walls, or by runners coupled to the top edges of the first and second side walls. The visualization device may be slideably disposed in a reservoir of a loading tray.

2 Claims, 5 Drawing Sheets

(56) References Cited

U.S. PATENT DOCUMENTS

| | | | | |
|---|---|---|---|---|
| 6,735,022 B1* | 5/2004 | Solitt | ..................... | A47F 7/02 |
| | | | | 206/566 |
| 7,134,735 B2 | 11/2006 | Cummins | | |
| 7,762,555 B1* | 7/2010 | Hofferber | ................. | A63F 1/10 |
| | | | | 273/148 A |
| 8,464,730 B1* | 6/2013 | Eng | ..................... | A45D 33/008 |
| | | | | 132/295 |
| 8,833,379 B1* | 9/2014 | Kaplan | ................. | A45D 33/26 |
| | | | | 132/287 |
| 2005/0145533 A1* | 7/2005 | Seligson | ............ | B65D 77/0446 |
| | | | | 206/575 |
| 2005/0173278 A1* | 8/2005 | Caron | ................... | A61B 50/30 |
| | | | | 206/370 |
| 2006/0219256 A1* | 10/2006 | Byun | ..................... | A45D 33/20 |
| | | | | 132/287 |
| 2006/0253048 A1* | 11/2006 | Jones | ............. | A61M 25/09041 |
| | | | | 600/585 |
| 2008/0149506 A1* | 6/2008 | Kuo | ....................... | B65D 43/18 |
| | | | | 206/235 |
| 2008/0236611 A1* | 10/2008 | Redzisz | ................ | A45C 5/005 |
| | | | | 132/315 |
| 2009/0044826 A1* | 2/2009 | Eng | ..................... | A45D 33/008 |
| | | | | 132/295 |
| 2009/0308782 A1 | 12/2009 | Grist | | |
| 2011/0264198 A1 | 10/2011 | Murray et al. | | |
| 2012/0103840 A1 | 5/2012 | McCaffrey | | |
| 2012/0150123 A1* | 6/2012 | Lawrence | ............ | A61M 5/158 |
| | | | | 604/180 |
| 2012/0305442 A1* | 12/2012 | Apodaca | .............. | A45D 33/006 |
| | | | | 206/581 |
| 2013/0056018 A1 | 3/2013 | Anderson-Stimson | | |

\* cited by examiner

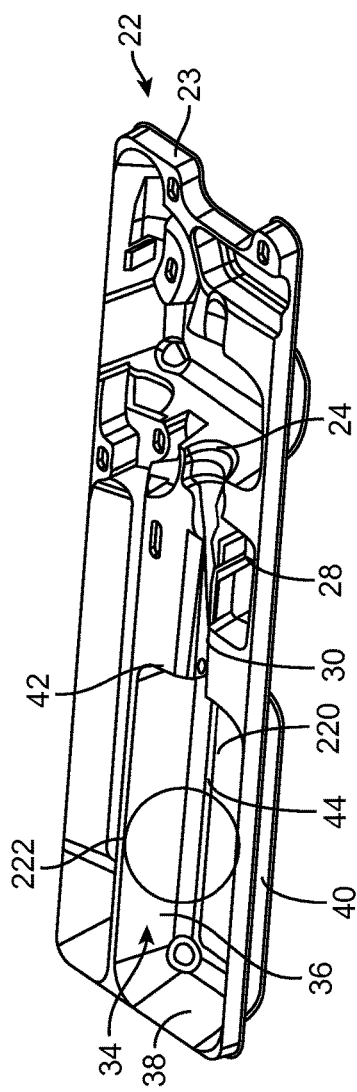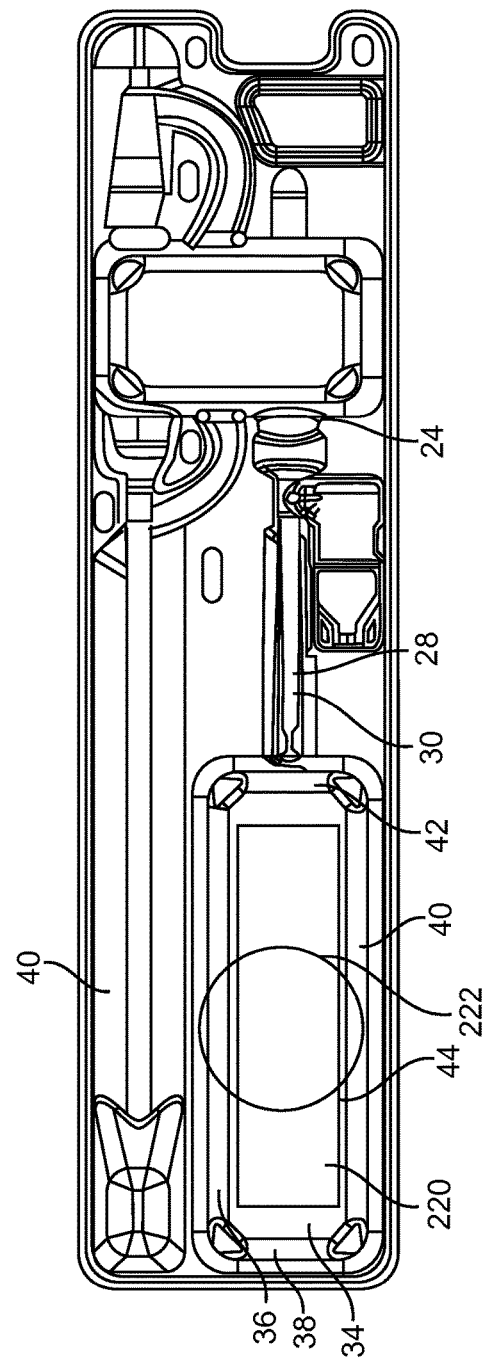
FIG. 4
FIG. 5

VISUALIZATION DEVICE FOR USE WITH A TRAY FOR LOADING A MEDICAL DEVICE

RELATED APPLICATIONS

This application is a Division of and claims the benefit of U.S. patent application Ser. No. 13/658,082, filed Oct. 23, 2012, now allowed. The disclosures of which are herein incorporated by reference in their entirety.

FIELD OF THE INVENTION

The present invention relates to catheter assemblies, loading trays, and methods of loading a catheter assembly. More specifically, the present invention relates to a visualization glass device for loading trays that improves the process of loading a medical device on a catheter assembly.

BACKGROUND

Heart valves, such as the mitral, tricuspid, aortic, and pulmonary valves, are sometimes damaged by disease or by aging, resulting in problems with the proper functioning of the valve. Heart valve problems generally take one of two forms: stenosis in which a valve does not open completely or the opening is too small, resulting in restricted blood flow; or insufficiency in which blood leaks backward across a valve when it should be closed.

Heart valve replacement has become a routine surgical procedure for patients suffering from valve regurgitation or stenotic calcification of the leaflets. Conventionally, the vast majority of valve replacements entail full stenotomy in placing the patient on cardiopulmonary bypass. Traditional open surgery inflicts significant patient trauma and discomfort, requires extensive recuperation times, and may result in life-threatening complications.

To address these concerns, within the last decade, efforts have been made to perform cardiac valve replacements using minimally-invasive techniques. In these methods, laparoscopic instruments are employed to make small openings through the patient's ribs to provide access to the heart. While considerable effort has been devoted to such techniques, widespread acceptance has been limited by the clinician's ability to access only certain regions of the heart using laparoscopic instruments.

Still other efforts have been focused upon percutaneous transcatheter (or transluminal) delivery of replacement cardiac valves to solve the problems presented by traditional open surgery and minimally-invasive surgical methods. In such methods, a valve prosthesis is compacted for delivery in a catheter and then advanced, for example through an opening in the femoral artery and through the descending aorta to the heart, where the prosthesis is then deployed in the valve annulus (e.g., the aortic valve annulus).

Valve prostheses are generally formed by attaching a bioprosthetic valve to a frame made of a wire or a network of wires. Such a valve prosthesis can be contracted radially to introduce the valve prosthesis into the body of the patient percutaneously through a catheter. The valve prosthesis can be deployed by radially expanding it once positioned at the desired target site. The valve prosthesis is mounted onto a distal tip of the catheter assembly prior to delivery to the target location where the valve prosthesis is expanded into place.

To prepare such a valve prosthesis for implantation, the valve prosthesis can be initially provided in an expanded or uncrimped condition, then crimped or compressed around the distal tip of the catheter assembly until the valve prosthesis is as close to the diameter of the distal tip as possible. Various methods and devices are available for crimping the valve prosthesis onto the catheter's distal tip, which may include hand-held devices or tabletop devices, for example. These crimping devices can initially provide an opening that is large enough to accommodate a valve prosthesis in its expanded condition and be positioned over a desired section of a distal tip of the catheter assembly. The valve prosthesis can then be compressed by reconfiguring the opening of the crimping device to uniformly decrease the size of the opening until the valve is compressed to the desired size. Due to the bioprosthetic valve, the valve prosthesis often is not shipped loaded into the delivery catheter. Instead, many trancatheter valve prostheses must be loaded into the catheter assembly by hand at the treatment facility (e.g., operating room) immediately prior to performance of the procedure.

Many transcatheter valve prostheses and corresponding catheter assemblies have connection or attachment points that the user/loader must ensure are connected during the loading procedure. If the connection points are not properly connected, there is a risk of premature detachment of the valve prosthesis from the catheter assembly. The user/loader may also need to observe that certain portions of the valve prosthesis are properly loaded into the catheter assembly. The connection points and other portions of the valve prosthesis which need to be observed during loading may be located at several locations around the circumference of the catheter assembly. For example, two connection points where the proximal (outflow) end of the valve prosthesis is connected to the catheter assembly may be disposed on opposite sides of the valve prosthesis. Further, the valve prosthesis is normally loaded in a liquid solution such as, but not limited to, a saline solution. Thus, a loading tray filled with such a liquid solution is often used for loading a valve prosthesis on a catheter assembly. The catheter assembly in some cases may be held in place by the loading tray or other devices while loading the valve prosthesis. Thus, in order to ensure that the connections and/or other observations on opposite sides of the catheter assembly are properly connected/observed, the catheter assembly and valve prosthesis must either be lifted out of the liquid solution and twisted, or the loader must try to make the connections without seeing all of the connections. Removing the valve prosthesis and catheter assembly out of the liquid solution during loading may introduce unwanted air bubbles into the assembly. Further, twisting the catheter assembly may damage the catheter assembly or the valve prosthesis.

According, there is a need for a device that allows the loader to observe all sides of the catheter assembly and prosthetic valve during loading of the prosthetic valve onto the catheter assembly.

SUMMARY OF THE INVENTION

Embodiments hereof relate to a visualization device for use with a loading tray. The visualization device includes a frame comprising a floor, a first side wall extending generally perpendicular from the floor, and a second side wall extending generally perpendicular from the floor and spaced from the first side wall. The visualization device further includes a mirror abutting the floor of the frame. A magnifying glass may also be supported by top edges of the first and second side walls, or by support runners coupled to the top edges of the first and second side walls.

Embodiments hereof also relate to a tray for loading a medical device on a catheter assembly. The loading tray includes a reservoir defined by a bottom surface, a first wall, a second wall, a third wall, a fourth wall, and a generally open top opposite the bottom surface. A mirror abuts the bottom surface of the reservoir and faces the open top. The mirror may be adhesively attached to the bottom surface. The mirror may be coupled to the bottom surface using a snap fit connection. A portion of the bottom surface may transparent and the mirror may be coupled to an underside surface of the bottom surface, wherein the underside surface faces away from the open top and the reflecting surface of the mirror is visible from the open top through the transparent portion of the bottom surface. A magnifying glass may be supported by the top edges of the first and third walls of the reservoir spanning a portion of the open top of the reservoir. The reservoir may be at least partially filled with a liquid solution.

Embodiments hereof also relate to a tray for loading a medical device on a catheter assembly. The loading tray includes a reservoir defined by a bottom surface, a first wall, a second wall, a third wall, a fourth wall, and a generally open top opposite the bottom surface. A frame is slideably disposed in the reservoir. The frame includes a floor abutting the bottom surface of the reservoir. The frame also includes a first side wall attached to the floor and extending generally perpendicular from the floor. The first side wall of the frame abuts the first wall of the reservoir. The frame also includes a second side wall attached to and extending generally perpendicular from the floor. The second side wall of the frame abuts the third wall of the reservoir. A mirror is coupled to the floor of the frame and faces the open top of the reservoir. A magnifying glass may also be supported by top edges of the first and second side walls of the frame, or by support runners coupled to the top edges of the first and second side walls of the frame.

BRIEF DESCRIPTION OF DRAWINGS

FIG. 4 is an exploded perspective view of a catheter assembly and a loading tray with another embodiment of a visualization device disposed in the loading tray.

FIG. 5 is a top view of the loading tray of FIG. 4.

DETAILED DESCRIPTION

Specific embodiments of the present invention are now described with reference to the figures, wherein like reference numbers indicate identical or functionally similar elements. Unless otherwise indicated, the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician. In addition, the term "self-expanding" is used in the following description with reference to one or more stent structures of the prostheses hereof and is intended to convey that the structures are shaped or formed from a material that can be provided with a mechanical memory to return the structure from a compressed or constricted delivery configuration to an expanded deployed configuration. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

The following detailed description is merely exemplary in nature and is not intended to limit the invention or the application and uses of the invention. Although the description of the invention is in the context of loading a heart valve prosthesis onto a catheter assembly, the devices and methods described herein can also be used for loading other devices onto catheter assemblies. Furthermore, there is no intention to be bound by any expressed or implied theory presented in the preceding technical field, background, brief summary or the following detailed description.

Figure 1:
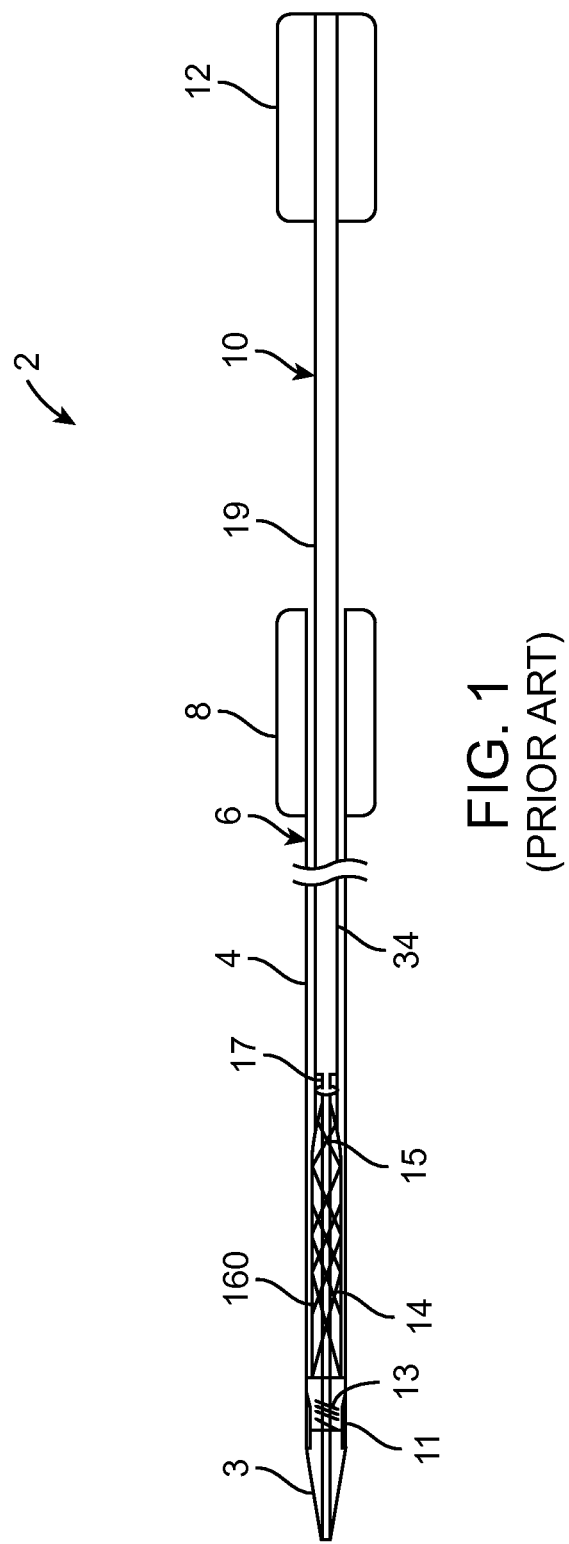
FIG. 1 is schematic diagram of a catheter assembly for delivering a transcatheter prosthetic heart valve to an implantation site, with the transcatheter heart valve prosthesis loaded in the catheter assembly.

FIG. 1 is a diagram illustrating an example of a catheter assembly 2 for delivering a transcatheter heart valve prosthesis 14 to an implantation site. In the illustrated example, catheter assembly 2 includes a shaft assembly 10 and a sheath assembly 6. The shaft assembly 10 includes a handle 12, a carrier shaft 19, a connector shaft 15, a distal tip assembly 3, a distal coupling structure 13, and a sleeve 11. The connector shaft 15 interconnects the carrier shaft 19 and the distal tip assembly 3, and in some constructions has a reduced-sized diameter to permit placement of a prosthetic heart valve 14 over the connector shaft 15. The distal tip assembly 3 is disposed at the distal end of the shaft assembly 10. Though not shown in FIG. 1, a guide wire lumen can be formed through shafts 15 and 19.

Carrier shaft 19 is sized to be slidably received within the sheath assembly 6, and is configured in the illustrated exampled for releasable coupling with the heart valve prosthesis 14. The carrier shaft 19 forms or includes a coupling device 17. The coupling device 17 is configured to selectively retain a proximal portion of the heart valve prosthesis 14. The coupling device 17 is configured to releasably mount the heart valve prosthesis 14 to the shaft assembly 10 when the heart valve prosthesis 14 is forced to a collapsed state within the sheath assembly 6. The sheath assembly 6 is configured to permit deployment of the heart valve prosthesis 14 from the loaded state shown in FIG. 1. The catheter assembly 2 is configured to transition from the loaded state in which the sheath assembly 6 encompasses the heart valve prosthesis 14 to a deployed state in which the sheath assembly 6 is withdrawn from the heart valve prosthesis 14.

The catheter assembly 2 shown in FIG. 1 is merely an example of delivery system that can be used to deliver a heart valve prosthesis transluminally to a desired treatment site. Further description of catheter assembly 2 can be found in U.S. Patent Application Publication No. 2011/0264198, the entirety of which is incorporated by reference herein. As shown, catheter assembly 2 includes coupling device 17 which selectively retains a proximal portion of heart valve prosthesis 14. As shown in FIG. 1, coupling device 17 includes two connections on opposite sides of carrier shaft. A user loading heart valve prosthesis 14 onto catheter assembly 2 must ensure that coupling device 17 and heart valve prosthesis 14 are properly connected at both connection points. Similarly, in a catheter assembly 2 such as shown in FIG. 1, the user must ensure that distal coupling structure 13 and heart valve prosthesis 14 are properly connected when loading prosthetic heart valve 14 onto catheter assembly 2.

Figure 2:
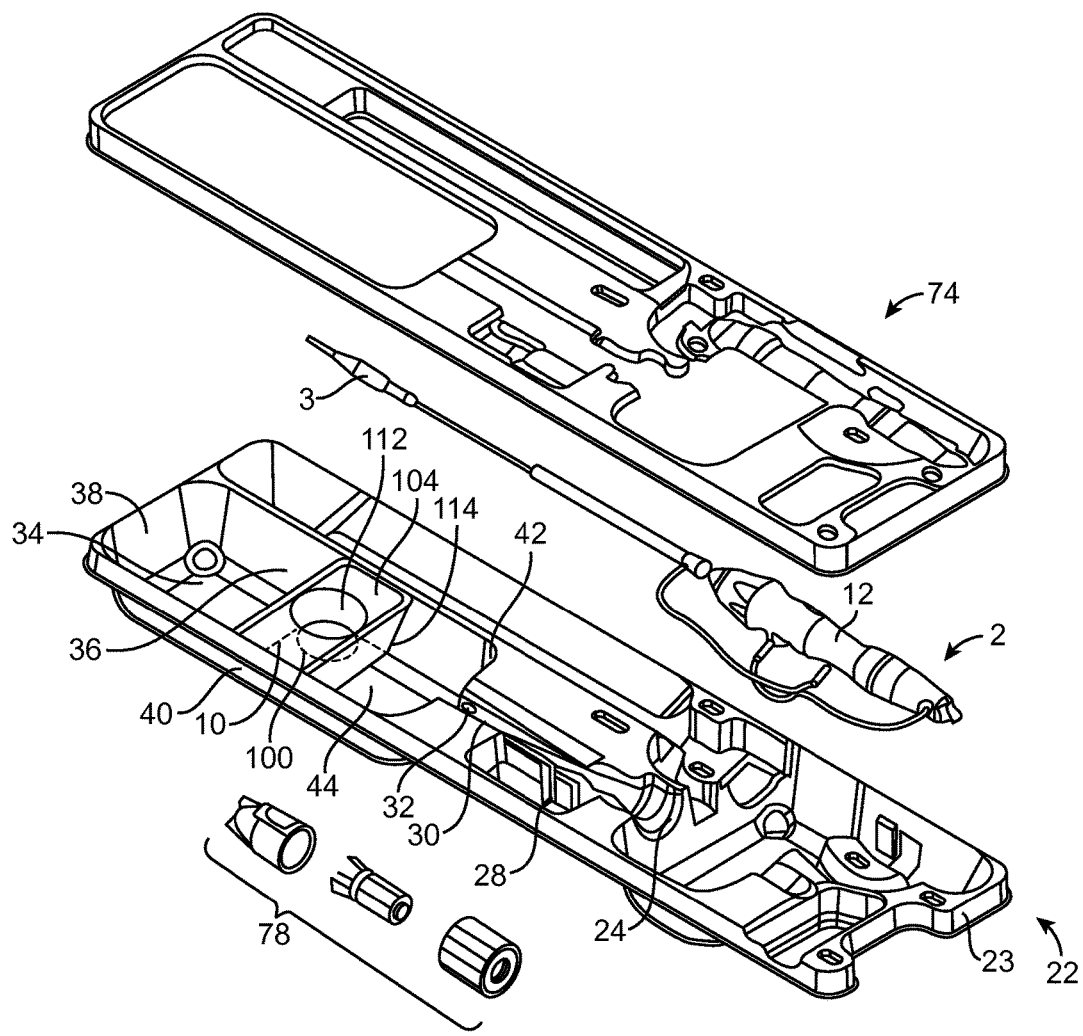
FIG. 2 is an exploded perspective view of a catheter assembly and a loading tray with visualization device disposed in the loading tray.

As discussed above, loading of heart valve prosthesis 14 onto catheter assembly 2 is generally performed in a liquid solution disposed in a reservoir of a loading tray. FIG. 2 shows an embodiment of a loading tray 22 including a visualization device 100. Other embodiments of the loading tray and visualization device are possible. Modifications can be made to the embodiments described herein without departing from the spirit and scope of the present invention. Therefore, the following detailed description is not meant to be limiting. Further, the systems and methods described below can be implemented in many different embodiments of hardware. Any actual hardware described is not meant to be limiting. The operation and behavior of the systems and methods presented are described with the understanding that modifications and variations of the embodiments are possible given the level of detail presented.

In the embodiment shown in FIG. 2, loading tray 22 is configured to be used with a catheter assembly 2 that may be similar to the catheter assembly 2 shown in FIG. 1. As described above, catheter assembly 2 generally includes a handle 12 located at a proximal end of catheter assembly 2, a distal tip assembly 3, and a sheath assembly 6 between distal tip assembly 3 and handle assembly 12. It is understood that catheter assembly 2 is merely an exemplary embodiment of a catheter assembly that can be used in conjunction with the devices described herein. Similarly, loading tray 22, described in detail below, is merely an exemplary embodiment of a loading tray that can be used in conjunction with the visualization device described herein. The present invention is not limited to visualization devices that can be used with loading trays and catheter assemblies as the one described herein. The visualization devices described herein can be used with loading trays having different configurations of reservoirs and receptacles, and with catheter assemblies having different types of handle assemblies, sheath assemblies, and distal tip assemblies.

Loading tray 22 will be described briefly herein in conjunction with the visualization devices described herein. Loading tray 22, however, can be any conventional loading tray adapted to include the visualization devices described herein. For example, and not by way of limitation, loading tray 22 can be the loading tray described in U.S. Patent Application Publication No. 2012/0103840, which is incorporated in its entirety by reference herein. Briefly, loading tray 22 is made of a tray body 23 defining a handle assembly receptacle 24 for seating handle assembly 12 of catheter assembly 2, an elongate delivery shaft receptacle 28 for seating sheath assembly 6 of catheter assembly 2, and a reservoir 34 for holding a fluid (not shown in FIG. 2). Tray body 23 can be made of various polymer or composite materials including, for example, Polyethylene Terephthalate Glycol (PETG). Tray body 23 can be molded and have a thickness of approximately 1.0-1.4 mm. The present invention, however, is not limited to polymer materials and can include other suitable materials, for example, stainless steel. A top surface 46 of tray body 23 generally defines the uppermost horizontal plane of loading tray 22.

Reservoir 34 has a bottom surface 44 that is below a portion of delivery shaft receptacle 28 that is contiguous with reservoir 34. When reservoir 34 is filled with a fluid and handle assembly 12 is seated in the handle assembly receptacle 24, distal tip assembly 3 is submerged in the fluid in reservoir 34.

In the present embodiment, reservoir 34 is defined by a right wall 36, a back wall 38, a left wall 40, and a front wall 42 that extend downward from top surface 46 to horizontal bottom surface 44 to form a rectangular recess. The depth of the reservoir 34 may vary depending upon the depth necessary to load a medical device on distal tip assembly 3 while submerged in the fluid in reservoir 34. For example, when loading tray 22 is used to load a heart valve prosthesis on catheter assembly 2, the depth of reservoir 34 can be approximately 62-68 mm. Although reservoir 34 is rectangular in the illustrated embodiment, the present invention includes a tray that defines reservoirs having other shapes, for example, hemispheres, squares, and cylinders.

In an embodiment, loading tray 22 may also include a cover 74, as shown in FIG. 2. Further, a crimping device 78 can be stored in loading tray 22 for delivery. Similarly, the loading tray may be modified to accommodate any of the visualization devices described in the embodiments below such that the visualization devices may be shipped with the loading tray, crimping device, catheter, medical device, and/or other devices associated with the procedure for which catheter is intended. Other features of loading tray 22 shown in FIG. 2 are not described herein, but are explained in U.S. Patent Application Publication No. 2012/0103840, which is incorporated in its entirety by reference herein.

Figure 3:
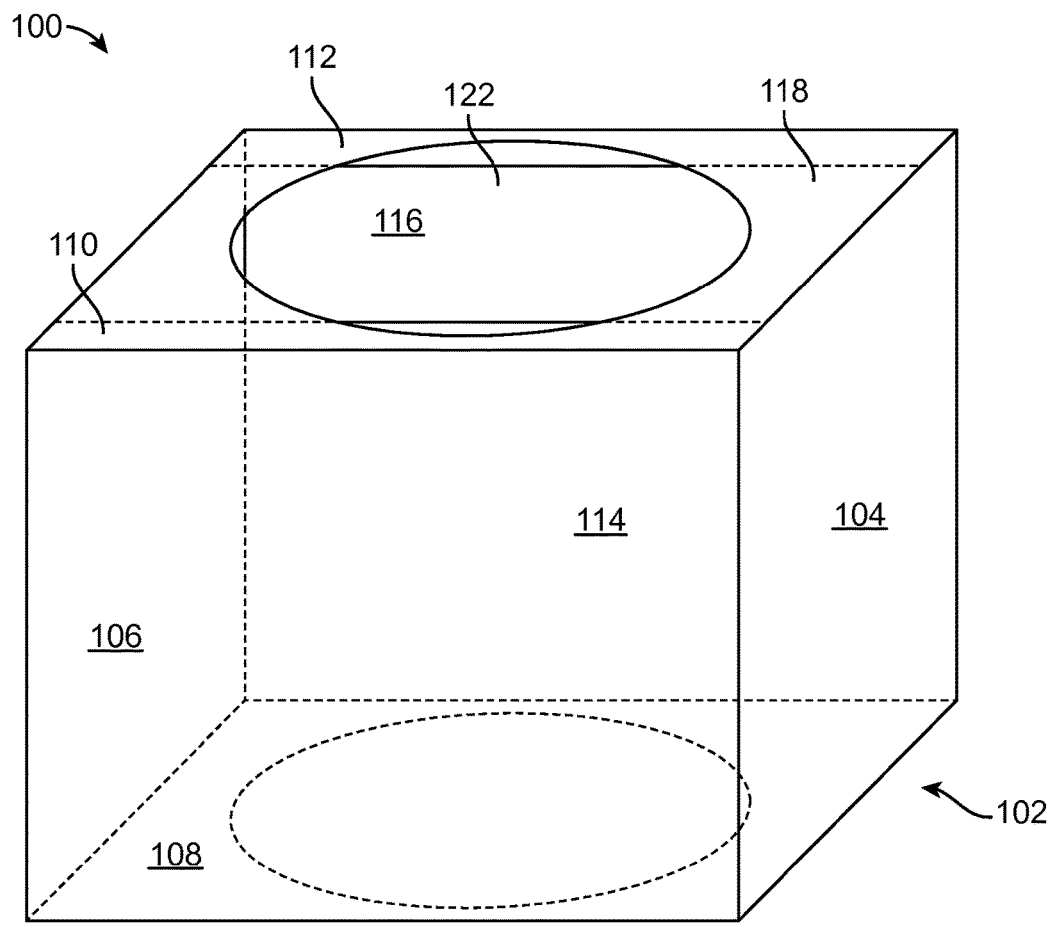
FIG. 3 is a perspective view of an embodiment of a visualization device.

In the embodiment shown in FIG. 2, a visualization device 100 is disposed within reservoir 34 of loading tray 22. Visualization device 100 allows for easier visualization of the portion of catheter assembly 2 facing bottom surface 44 of reservoir 34. In the embodiment of FIGS. 2 and 3, visualization device 100 is not attached to loading tray 22 such that visualization device 100 can slide within reservoir 34 to allow the user to visualize different parts of catheter assembly 2 and heart valve prosthesis 14 while loading heart valve prosthesis 14 onto catheter assembly 2. However, visualization device in other embodiments could be attached or otherwise coupled to loading tray 22, as described in more detail below.

FIG. 3 shows a perspective view of an embodiment of visualization device 100. Visualization device 100 includes a frame 102 with a right wall 104, a left wall 106, and a floor or bottom surface 108. Right and left walls 104, 106 are attached to and extend generally perpendicularly away from floor 108. Frame 102 also includes a front support runner 110 and a back support runner 112 spanning a portion of an open top 118 of frame 102. Frame 102 includes an open front 114 and an open back 116. The terms "left", "right", "front", "back", "top", and "bottom" as used with respect to visualization device 100 do not limit visualization device 100 to any particular orientation. Instead, the terms as used with respect to visualization device 100 are intended to be consistent with the manner in which the terms are used to describe the walls of reservoir 34 of loading tray 22. Further, when referring to the "open top", "open front", and "open back" of the frame, those skilled in the art would recognize that these refer to planes between the walls that allow for a user to access the area. Further, these areas need only be generally open in that there can be some support at the edges of the open plane provided that the user can access the catheter assembly through the open front and open back of the frame.

Accordingly, when visualization device 100 is placed into reservoir 34 of loading tray 22, as shown in FIG. 2, right wall 104 of frame 102 is disposed adjacent or against right wall 36 of reservoir 34, left wall 106 of frame 102 is disposed adjacent or against left wall 40 of reservoir 34, and floor 108 of frame 102 is disposed adjacent or against bottom surface 44 of reservoir 34. Similarly, open top 118 is oriented in the direction of top 46 of loading tray 22, open front 114 is oriented in the direction of front wall 42 of reservoir 34, and open back 116 is oriented in the direction of back wall 38 of reservoir. Also, front support runner 110 spanning a portion of open top 118 is disposed near the intersection of open front 114 and open top 118 and back support runner 112 spanning a portion of open top 118 is disposed near the intersection of open back 116 and open top 118. Front and back support runners 110, 112 are coupled to or rest on top edges of right wall 104 and left wall 106, and span the distance between right and left walls 104, 106. The walls of frame 102 may be formed from a clear plastic material, such as an acrylic material. However, any material may be used that is suitable for the purpose of frame 102, as described in more detail below.

A mirror 120 is coupled to floor 108 of frame 102. Mirror 120 can be a conventional mirror or can be a mirror with magnification. As used herein, the term "mirror" means a reflecting surface such as, but not limited to, a polished metal or glass with a silvery, metallic, or amalgam backing. In one non-limiting example, mirror 120 has two-times magnification. Mirror 120 may be coupled to floor 108 by any means known to those skilled in the art. For example, and not by way of limitation, mirror 120 may be coupled to bottom surface 108 using an adhesive. In another example, mirror 120 may simply abut floor 108 such that the weight of mirror 120 keeps mirror 120 abutting against floor 108 when visualization device 100 is disposed in reservoir 34. Further, a magnifying glass 122 may rest against front and back support runners 110, 112 of open top 118 of frame 102. Alternatively, front and back runners 110, 112 may be excluded and magnifying glass 122 may rest against top edges of left and right walls 104, 106. Magnifying glass 122 may be coupled to front and back support runners 110, 112, such as by an adhesive, but such coupling is not necessary. Magnifying glass 122 may magnify at any desirable, for example, but not limited to, two times magnification.

In a method of using visualization device 100 with loading tray 22, visualization device 100 is placed in reservoir 34 such that right and left walls 104, 106 of visualization device 100 abut right and left walls 36, 40 of reservoir 34 and floor 108 of visualization device abuts bottom surface 44 of reservoir 34. The catheter assembly 2 is placed in tray 22 such that tip assembly 3 is placed in a liquid solution which fills at least a portion of reservoir 34. Catheter assembly is extended through open front 114 and open back 116 of frame 102 such that the tip assembly 3 is located between open top 118 and floor 108 of frame 102. Magnifying glass 122 may or may not be disposed on front and back support runners 110, 112 of frame 102 such that the user looks through magnifying glass 122 to see tip assembly 3 of catheter assembly 2. The user can look at mirror 120 on floor 108 of frame 102 to see a reflection of the portion of tip assembly 3 facing away from open top 118 of frame 102 (i.e., portion facing mirror 120). Accordingly, when loading heart valve prosthesis 14 onto catheter assembly 2, generally near tip assembly 3, the user can directly see the portion of the catheter assembly facing top 118 and see a reflection of the portion of the catheter assembly 2 facing mirror 120 in mirror 120. This permits the user to see any connections on the portion of the catheter assembly 2 facing mirror 120 without having to twist catheter assembly 2 or lift catheter assembly 2 out of the liquid solution in reservoir 34. This also permits the user to observe the portion of catheter assembly facing mirror 120 to ensure that the heart valve prosthesis 14 is properly loaded onto catheter assembly 2.

FIGS. 4-5 show another embodiment of a loading tray 22 with a visualization device at least partially incorporated into the loading tray 22. Loading tray 22 will not be described in detail as the features therein are the same as in FIG. 2 except where specifically described herein with respect to FIGS. 4-5. In particular, instead of a separate frame as described in FIGS. 2-3, a mirror 220 is incorporated into bottom surface 44 of tray 22. Mirror 220 may be a separate piece coupled to bottom surface 44, or can be formed integral with bottom surface 44. For example, and not by way of limitation, mirror 220 may be adhesively attached to bottom surface 44 such that mirror 220 faces the open top of reservoir 34. Mirror 220 may be coupled to bottom surface 44 of reservoir 34 in other ways such that a user utilizing tray 22 can see a reflection in the mirror 220 showing an underside of a catheter disposed within reservoir. For example, and not by way of limitation, mirror 220 may be snap fit into clips or other mechanism on bottom surface 44, or press fit onto bottom surface 44. In another non-limiting example, at least a portion of bottom surface 44 of reservoir 34 may be transparent and mirror 220 may be coupled to an underside of bottom surface 44, such as by adhesive, a snap fit or a press fit arrangement. In another non-limiting example, bottom surface 44 of reservoir 34 may be made of a reflecting material or a reflecting material may be added to bottom surface 44. For example, and not by way of limitation, aluminum oxide may be vapor deposited onto bottom surface 44 to make bottom surface reflective. As shown, mirror 220 covers substantially all of bottom surface 44 of reservoir 34. However, mirror 220 can be any suitable size such that mirror 220 can be used to observe a side of the catheter assembly facing mirror 220 when a portion of the catheter assembly is disposed in the reservoir. Mirror 220 may or may not include magnification. For example, and not by way of limitation, mirror 220 may have two times magnification to make it easier for the user to see the desired portions of the catheter assembly and heart valve prosthesis.

Further, a magnifying glass 222 can be used in conjunction with mirror 220. Magnifying glass 222 may rest on top surface 46 of tray at left and right walls 36, 40 of reservoir 34. Magnifying glass 222 may be coupled to top surface 46, such as by an adhesive, or may be provided separate from tray 22 such that magnifying glass 222 can be moved to the desired area by the user. Magnifying glass 222 may have any magnification desirable for use in assisting a user load a prosthetic heart valve onto a catheter assembly. For example, and not by way of limitation, magnifying glass 222 may have two times magnification.

Figure 6:
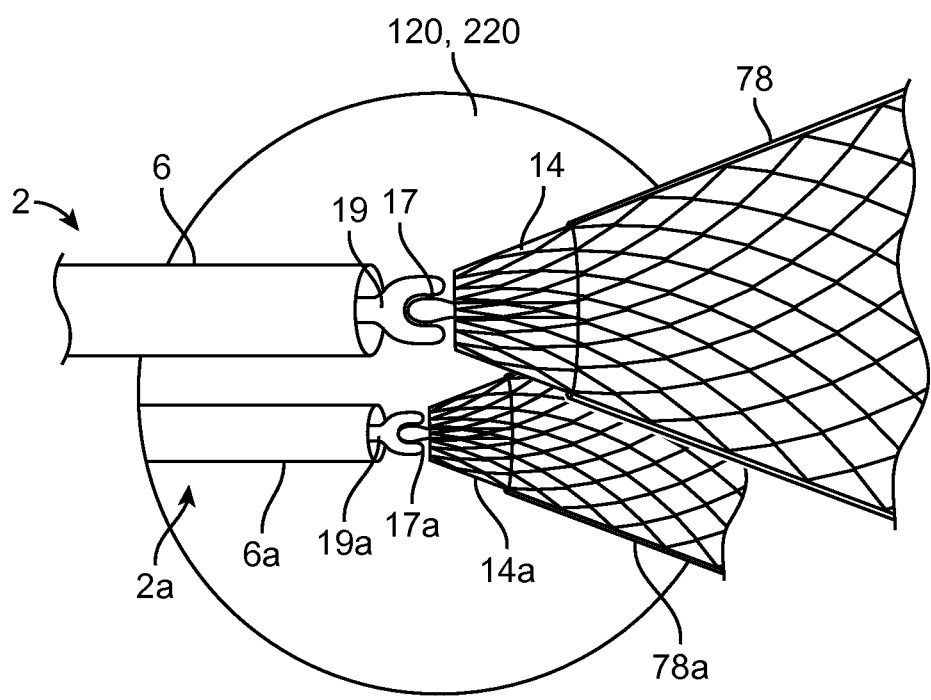
FIG. 6 is a perspective view of a portion of a catheter assembly with a heart valve prosthesis being loaded therein as seen through a visualization device as described herein.

FIG. 6 shows an illustration of heart valve prosthesis 14 being loaded onto a catheter assembly 2 as seen using a visualization device as described herein. In FIG. 6, the reference numerals ending in "a" are as reflected in mirror 120, 220. In particular a crimper 78 is used to load heart valve prostheses 14 onto catheter assembly 2 within sheath assembly 6. Coupling device 17 couples shaft 19 to heart valve prosthesis 14. As can be seen in FIG. 6, a user must observe that the coupling device 17 is connected to heart valve prosthesis 14 along a direct line of vision of the user and in the reflection at 17a. As the heart valve prosthesis 14 continues to be loaded onto catheter assembly 2, the user can observe that the heart valve prosthesis is smoothly crimped within sheath 6 on both a direct line of vision and as reflected in mirror 120, 220.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. It will also be understood that each feature of each embodiment discussed herein, and of each reference cited herein, can be used in combination with the features of any other embodiment. All patents and publications discussed herein are incorporated by reference herein in their entirety.

What is claimed is:

1. A tray for loading a medical device on a catheter assembly, the tray comprising:
   a reservoir defined by a bottom surface, a first wall, a second wall, a third wall, and a fourth wall, the reservoir having a generally open top opposite the bottom surface, wherein the bottom surface includes a reflecting surface facing the open top; and
   a magnifying glass spanning a portion of the open top of the reservoir, wherein the magnifying glass rests on an edge of the first wall of the reservoir and an edge of the third wall of the reservoir.

2. A tray for loading a medical device on a catheter assembly, the tray comprising:
   a reservoir defined by a bottom surface, a first wall, a second wall, a third wall, and a fourth wall, the reservoir having a generally open top opposite the bottom surface, wherein the bottom surface includes a reflecting surface facing the open top, wherein the reservoir is at least partially filled with a liquid solution.

* * * * *